United States Patent [19]

Gregory et al.

[11] 3,991,067

[45] Nov. 9, 1976

[54] MONO- OR DISUBSTITUTED 1,2,4,OXADIAZOLES WHICH ARE SUBSTITUTED BY AT LEAST 1-N-SUBSTITUTED CARBAMOYL GROUP

[75] Inventors: Gordon Ian Gregory, Chalfont St. Peter; William Kingston Warburton; Peter William Seale, both of Pinner, all of England

[73] Assignee: Glaxo Laboratories Limited, Greenford, England

[22] Filed: Nov. 13, 1973

[21] Appl. No.: 415,342

Related U.S. Application Data

[63] Continuation-in-part of Ser. No. 253,807, May 16, 1972, abandoned.

[30] Foreign Application Priority Data

May 19, 1971 United Kingdom............... 15838/71

[52] U.S. Cl....................... 260/293.67; 260/240 R; 260/240 A; 260/240 D; 260/240.1; 260/247.1 L; 260/247.1 M; 260/247.2 A; 260/247.5 E; 260/268 C; 260/293.62; 260/294.8 R; 260/294.8 G; 260/294.9; 260/295 K; 260/295 AM; 260/307 F; 260/332.3 R; 260/347.7; 260/564 G; 260/296 R; 424/248; 424/250; 424/263; 424/267; 424/272
[51] Int. Cl.$^2$........................................ C07D 271/06
[58] Field of Search....... 260/307 G, 293.67, 268 C, 260/247.2 A, 247.1 M, 247.5 E, 295 AM

[56] References Cited
UNITED STATES PATENTS

| | | | |
|---|---|---|---|
| 3,478,049 | 11/1969 | Von Esch et al. | 260/307 |
| 3,720,668 | 3/1973 | Breuer | 260/240 A |

FOREIGN PATENTS OR APPLICATIONS

| | | |
|---|---|---|
| 80,217 | 7/1969 | Germany |
| 85,778 | 11/1971 | Germany |

OTHER PUBLICATIONS

Ruccia et al.—C.A. 69, 77174s (1968).
Strani et al.—Gazz. Chim. Ital. 93, 482–484 (1963).

*Primary Examiner*—Raymond V. Rush
*Attorney, Agent, or Firm*—Bacon & Thomas

[57] ABSTRACT

1,2,4-Oxadiazoles having as 3- and 5-substituents a hydrogen atom, an aliphatic, cycloaliphatic, araliphatic, aryl or heterocyclic group, or a carbamoyl group of the formula — $CONR^1R^2$ where $R^1$ & $R^2$ which can be the same or different, are hydrogen atoms or aliphatic, cycloaliphatic, araliphatic or aryl groups or, taken with the N atom, a heterocyclic ring; provided that at least one of the 3- or 5-substituents is an N-substituted carbamoyl group. Antimicrobial activity, and particularly antiviral, antiparasitic and antibacterial activity is shown in this group. The corresponding oxadiazolins are also described and are useful intermediates in the preparation of the oxadiazoles.

9 Claims, No Drawings

MONO- OR DISUBSTITUTED 1,2,4,OXADIAZOLES WHICH ARE SUBSTITUTED BY AT LEAST 1-N-SUBSTITUTED CARBAMOYL GROUP

This application is a continuation-in-part of application Ser. No. 253,807 of Gregory et al., filed May 16, 1972 now abandoned.

This invention relates to new oxadiazole derivatives, processes for the preparation thereof and pharmaceutical compositions containing the same.

We have found that interesting physiological activity, particularly antimicrobial activity, including antiviral, antiparasitic and antibacterial activity, is shown by a group of 3 and/or 5-substituted 1,2,4-oxadiazole compounds.

In one aspect the invention provides novel 1,2,4-oxadiazole compounds of the general formula

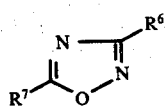   I where $R^6$ represents R, where R represents a hydrogen atom or an aliphatic, cycloaliphatic, araliphatic, aryl or heterocyclic group; or a carbamoyl group of the formula —$CONR^1R^2$ where $R^1$ and $R^2$, which may be the same or different, represent hydrogen atoms, aliphatic, cycloaliphatic, araliphatic or aryl groups or, together with the intervening N, represent a heterocyclic ring; and $R^7$ represents R, where R is as defined above or a carbamoyl group of the formula —$CONR^3R^4$, where $R^3$ and $R^4$ are as defined for $R^1$ and $R^2$; provided that at least one of $R^6$ and $R^7$ is an N-substituted carbamoyl group.

Thus, for example, R may represent an aryl group which is preferably mono- or bi-cyclic, such as a phenyl, naphthyl or biphenylyl group; or an araliphatic group such as an aralkyl, aralkenyl or aralkynyl group e.g. a benzyl, phenethyl, phenylethynyl or styryl group. R may alternatively represent a heterocyclic group, e.g. a 5- or 6-membered group such as a furyl, thienyl or pyridyl group. Such aryl, araliphatic and heterocyclic groups may carry one or more ring substituents such as lower alkyl, lower alkoxy, lower alkylthio, lowr alkylsulphinyl, lower alkylsulphonyl, amino, acylamino, cyano, thiocyanato or nitro groups or halogen atoms, for example, a tolyl, p-methoxyphenyl, p-nitrophenyl, p-chlorophenyl, p-methylthiostyryl, p-methylsulphinylstyryl or p-methoxystyryl group. The acyl portions of the acylamino may for example be straight or branched lower alkanoyl groups. When an amino ring substituent is present the compounds may form salts e.g. with strong acids such as hydrochloric and sulphuric acid. Where R represents an aliphatic group this may for example be an alkyl, alkenyl or alkynyl group such as a methyl or ethyl group, an allyl group, an ethynyl group or a propargyl group, which may carry heterocyclic groups as substituents e.g. 5- or 6-membered groups such as furyl, thienyl or pyridyl groups which may themselves carry substituents.

When R is an aliphatic group it is preferably saturated. Where R is a heterocyclic group or carries a heterocyclic substituent, the hetero atom(s) is preferably S and/or N, and the group is preferably not a nitrofuryl group.

Where R is a cycloaliphatic group this may for example be a cycloalkyl group having 3–10 carbon atoms, e.g. a cyclohexyl group.

$R^1$, $R^2$, $R^3$ and $R^4$ may, for example, represent aliphatic groups which may be substituted by functional groups such as hydroxy groups, especially lower alkyl groups such as methyl, ethyl, propyl, n-butyl, t-butyl or 2-hydroxyethyl groups, alkenyl groups such as allyl groups or alkynyl groups such as a propargyl group; aryl groups especially monocyclic aryl groups such as phenyl groups, which may carry one or more alkyl or alkoxy substituents; aralkyl, aralkenyl or aralkynyl groups especially monocyclic groups such as benzyl groups or cycloaliphatic groups especially monocyclic cycloalkyl groups such as cyclohexyl groups or caged cycloalkyl groups such as adamantyl groups. $R^1$ and $R^2$ or $R^3$ and $R^4$ may together with the intervening N represent a substituted or unsubstituted nitrogen-containing heterocyclic group, which may contain a further hetero atom such as oxygen or nitrogen, e.g. a piperidino, morpholino, pyrrolidin-1-yl, piperazin-1-yl, 4-lower-alkylpiperazin-1-yl or 3-azabicyclo-(3,2,2)-nonan-3-yl group. These heterocyclic groups may be substituted e.g. by the substituents described above for heterocyclic R groups.

In general each of the substituents R, $R^1$, $R^2$, $R^3$ and $R^4$ preferably has less than 20 carbon atoms; aliphatic groups preferably have up to 6 carbon atoms and alkyl, alkenyl and alkynyl portions of aralkyl, aralkenyl or aralkynyl groups preferably have up to 6 carbon atoms. Heterocyclic groups preferably have 5–10 ring members. Cycloalkyl groups preferably have 3–10, especially 3–7, carbon atoms.

It will be understood from the above that preferred compounds in accordance with the invention are generally compounds of the formula I wherein: $R^6$ represents R, where R is hydrogen; an alkyl, alkenyl, or alkynyl group containing up to 6 carbon atoms or such a group substituted with a furyl, thienyl, or pyridyl group; a cycloalkyl group having 3–10 carbon atoms; a phenyl, naphthyl, biphenylyl, benzyl, phenethyl, phenylethynyl, styryl, furyl, thienyl or pyridyl group or such a group substituted with one or more lower alkyl, lower alkoxy, lower alkylthio, lower alkylsulphinyl, lower alkylsulphonyl, amino, lower alkanoyl amino, cyano, thiocyanato or nitro groups or a halogen atom; or a carbamoyl group of the formula —$CONR^1R^2$, where $R^1$ and $R^2$ which may be the same or different each represents hydrogen, an alkyl, alkenyl, or alkynyl group containing up to 6 carbon atoms or such a group substituted by hydroxy; phenyl or phenyl substituted with one or more alkyl or alkoxy substituents; benzyl; cycloalkyl containing 3–10 carbon atoms; a caged cycloalkyl group; or, together with the intervening nitrogen atom, represent a piperidino, morpholino, pyrrolidin-1-yl, piperazin-1-yl, 4-lower-alkylpiperazin-1-yl, or 3-azabicyclo-(3,3,2)-nonan-3-yl group or such a group substituted by one or more lower alkyl, lower alkoxy, lower alkylthio, lower alkylsulphinyl, lower alkylsulphonyl, amino, lower alkanoylamino, cyano, thiocyanato, or nitro groups or a halogen atom; and $R^7$ represents R, where R is as defined above, or a carbamoyl groups of the formula —$CONR^3R^4$, where $R^3$ and $R^4$ are as defined above for $R^1$ and $R^2$; provided that at least one of $R^6$ and $R^7$ is an N-substituted carbamoyl group.

Particularly preferred, by virtue of their physiological activity, are those compounds of the general formula I in which R represents an aryl group, especially a bicyclic and/or substituted aryl group, or an araliphatic group, which may also be substituted. The preferred R groups thus possess at least 7 carbon atoms. Preferred examples of substituents which may be present on aryl or araliphatic groups are alkyl (e.g. $C_{1-6}$ alkyl), alkoxy (e.g. $C_{1-6}$ alkoxy), alkylsulphinyl or alkylthio (e.g. $C_{1-6}$ alkyl), thiocyanato or nitro groups, and halogen atoms. Examples of such R groups are a tolyl, α-naphthyl, biphenylyl, p-methoxyphenyl, p-chlorophenyl, p-methylsulphinylstyryl or p-methylthiostyryl group, or a hydrogen atom. Carbamoyl groups of particular interest, especially when an R group as just mentioned is also present, are those in which $R^1$, $R^2$, $R^3$ or $R^4$ represents an adamantyl group, or wherein $R^1$ and $R^2$ or $R^3$ and $R^4$ are both methyl, ethyl or n-propyl groups or, together with the intervening nitrogen atom, a nitrogen-containing heterocyclic group e.g. a piperidino group such as described above.

The compounds of formula I may be prepared by any convenient method, in particular by reaction of a compound of the general formula

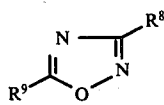
II (where $R^8$ and $R^9$, which may be the same or different, represent R as defined above, a group of the formula —$CONR^1R^2$ or —$CONR^3R^4$ as defined above or a carboxylic acid group or a reactive derivative thereof, provided that at least one of $R^8$ and $R^9$ represents a carboxylic acid group or a reactive derivative thereof) with a nitrogen base of the formula $R^1R^2NH$ or $R^3R^4NH$ (where $R^1$, $R^2$, $R^3$ and $R^4$ are as defined above) or, where a carboxylic acid of formula II is used, with an isocyanate of the formula $R^1NCO$ or $R^3NCO$.

The reactive derivative may be, for example, an ester or an acid halide, e.g. chloride, symmetrical or mixed anhydride or azide. The reactive derivatives are most conveniently the alkyl esters having 1–6 carbon atoms in the alkoxy moiety, e.g. the methyl or ethyl ester; araliphatic esters e.g. the benzyl ester; or aryl esters, e.g. p-nitrophenyl or p-chlorophenyl esters.

Where the compound of formula II is base-sensitive, e.g. when $R^8$ or $R^9$ is hydrogen, it is preferred to use an acid azide or halide, e.g. chloride, as reactive derivative. Such acid chlorides or azides may conveniently be prepared from the corresponding esters via the hydrazides. Where the reactive derivative is an ester, this is conveniently reacted with an excess of the nitrogen base either alone or in an inert solvent such as an alcohol, e.g. ethanol or methanol, a cyclic ether such as dioxan, a hydrocarbon solvent, such as toluene or a halogenated hydrocarbon solvent such as chloroform. The reaction is preferably effected at the reflux temperature of the system.

Reaction of the acid azide or halide is desirably effected in an inert solvent, e.g. a halogenated hydrocarbon solvent such as chloroform or an ester such as ethyl acetate, at ambient temperature. Where using an acid halide, an acid-binding agent is preferably present, e.g. pyridine, propylene oxide or triethylamine.

The amide formation can also be effected by reacting a carboxylic acid of formula II with the nitrogen base in the presence of a water-abstracting agent e.g. a diimide such as dicyclohexylcarbonyldiimide or carbonyldiimidazole; or alternatively with an isocyanate $R^1NCO$ or $R^3NCO$ giving a product in which $R^6$ and/or $R^7$ represents —$CONHR^1$ or —$CONHR^3$ respectively.

The 1,2,4-oxadiazole ring system itself can be synthesised using any convenient method.

In particular, the compounds of formula II and certain products of formula I can be prepared from correspondingly substituted amidoximes employing O-acylation and subsequent cyclisation, for example, using acid halides, anhydrides, azides, amides, esters or orthoesters. The acylation may be carried out where necessary in the presence of an acid binding agent such as pyridine, propylene oxide or triethylamine.

In one embodiment of this method, an amidoxime of the formula

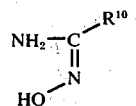
III (where $R^{10}$ represents R as defined above) is reacted with an oxalic acid derivative of the formula HalCOX where Hal represents a halogen atom, especially chlorine, and X a group —$CONR^3R^4$ or an esterified carboxylic acid group, as described in relation to $R^8$ and $R^9$, for example a lower ($C_{1-6}$) alkoxycarbonyl group, e.g. an ethoxycarbonyl group, to yield either (a) a product of the formula I in which $R^6$ represents R and $R^7$ represents a group of the formula $CONR^3R^4$ or (b) an intermediate of the formula II in which $R^8$ represents R and $R^9$ represents an esterified carboxylic acid group.

In another embodiment of the method an amidoxime of the formula III, where $R^{10}$ represents an esterified carboxylic acid group, is reacted with the derivative of formula HalCOX as defined above to yield an ester of the formula II in which $R^8$ represents an esterified carboxylic acid group and $R^9$ represents an esterified carboxylic acid group or a group of the formula —$CONR^3R^4$. The reaction is advantageously carried out in the presence of an acid binding agent, such as pyridine, propylene oxide or triethylamine.

In a further embodiment an amidoxime of the formula III in which $R^{10}$ represents an esterified carboxylic acid group is reacted with an acid halide of the carboxylic acid $RCO_2H$ where R is as defined above yielding an ester of the formula II where $R^8$ represents an esterified carboxylic acid group and $R^9$ represents R as defined above. The reaction is advantageously carried out in the presence of an acid binding agent, such as pyridine, propylene oxide or triethylamine.

Alternatively the amidoxime of formula III where $R^{10}$ represents R, an esterified carboxylic acid group or a group —$CONR^1R^2$ is reacted with a glyoxylic acid derivative of the formula HCO X where X is as defined above to yield an oxadiazoline of formula

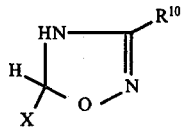

which may be oxidised to give the corresponding oxadiazole of formula II, or where X and/or $R^{10}$ represents an esterified carboxylic acid group, may be reacted with an amine $HNR^3R^4$ to give an oxadiazoline of formula

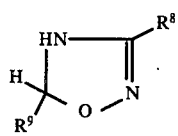

where $R^8$ represents R as defined above or a group $—CONR^1R^2$ and $R^9$ represents a group $—CONR^3R^4$ as defined above. Where $R^{10}$ and X both represent an esterified carboxylic acid group, $R^8$ in the product formed of formula V represents a group $CONR^1R^2$ where $R^1$ and $R^2$ are identical to $R^3$ and $R^4$ in $R^9$. These oxadiazolines (and those wherein $R^9$ represents R) can be oxidised to yield a product of formula I and are themselves of interest as intermediates and accordingly form a further feature of the present invention.

Compounds of the formula II (in which $R^9$ represents a hydrogen atom and $R^8$ represents an esterified carboxylic acid group) or compounds of formula I (in which $R^7$ represents a hydrogen atom and $R^6$ represents a group $—CONR^12^2$) may be prepared by reacting an amidoxime of formula III, where $R^{10}$ represents an esterified carboxyl group or a group $—CONR^1R^2$, with an orthoformate, e.g. triethyl or trimethyl orthoformate in the presence of a Lewis acid such as boron trifluoride or its etherate; or with formyl fluoride, conveniently at reduced temperature e.g. $-78°$ to room temperature, in an inert solvent. Alternatively, this reaction may be carried out with a Meerwein reagent (e.g. a dialkyl acetal of dimethylformamide) or the Wilsmeier-Haack reagent (phosphorus oxychloride and dimethylformamide).

In general, the preparation of a compound of formula I or formula II, whether substituted or unsubstituted at the 5-position, from an amidoxime of formula III may be effected in an inert solvent. Alternatively an excess of the reagent may be used, for example when using an orthoformate as reagent. Where acid halides are used, halogenated hydrocarbon solvents such as chloroform are particularly suitable and an acid-binding agent is preferably present, e.g. pyridine, propylene oxide or triethylamine.

The reaction with the amidoxime is conveniently effected at an ambient temperature or a moderately elevated temperature, for example the reflux temperature of the system.

The oxidation of an oxadiazoline to an oxadiazole is conveniently effected, for example, using manganese dioxide, potassium or sodium permanganate, sodium nitrite, ferric chloride, palladised charcoal and air, chloranil or related quinones. This reaction is conveniently effected in a solvent the nature of which will depend upon the oxidising agent used. Suitable solvents include for example methanol, chloroform and ethyl acetate.

The temperature at which the oxidation is carried out will also depend on the oxidising agent used but will generally be between 0° to 100° C.

It will be appreciated that for compounds of the formula I in which R represents an aryl or araliphatic group carrying a substituent, it may be preferable first to prepare a compound of formula I having a different substituent by a method as set forth above, which substituent is thereafter converted into the desired substituent. Thus for example, if it is desired that R be an aminophenyl or a cyanophenyl group, it is convenient first to prepare a compound in which R is nitrophenyl, the nitro group being then reduced to an amino group, which latter may then, if desired, be converted to, for example, a cyano group or halogen atom e.g. by a Sandmeyer reaction. Furthermore compounds bearing alkylsulphinyl and alkylsulphonyl groups in the group R may advantageously be prepared from the corresponding alkylthio compounds by oxidation, for example using peracetic acid or aqueous hydrogen peroxide; where it is desired to form an alkylsulphinyl group, in general approximately one equivalent of oxidising agent will be used.

It should further be noted that the oxidation of such substituents in the group R in a corresponding oxadiazoline ring can yield the oxadiazole product of formula I and this constitutes a variation of the oxidation method described above.

As stated above, interesting antiviral activity has been shown in the group of compounds in accordance with the invention, principally against Rhinovirus strains, particularly Rhinovirus Serotype 1 (previously known as M1), and Rhinovirus Serotype 9 (previously known as H9). 3-Adamantylcarbamoyl 1,2,4-oxadiazole has shown noteworthy activity against Influenza A2 and Herpes simplex viruses. The following Table I lists a number of compounds identified with respect to formula I having especially high activity against Rhinovirus, especially the Serotypes 1 and 9.

Table I

| $R^6$ | $R^7$ | Rhinovirus Serotype |
|---|---|---|
| $C_{10}H_7(\alpha)$ | $Et_2NCO$ | 1 |
| p-MeO-phenyl | $Et_2NCO$ | 1 |
| $CONMe_2$ | p-Cl-phenyl | 1 |
| $CONMe_2$ | $C_{10}H_7(\alpha)$ | 1 |
| trans-p-MeS-styryl | $Me_2NCO$ | 1, 9 |
| p-MeO-phenyl | piperidinocarbonyl | 1, 9 |
| $C_{10}H_7(\alpha)$ | piperidinocarbonyl | 1, 9 |
| p-MeO-phenyl | $Me_2NCO$ | 1 |
| $C_{10}H_7(\alpha)$ | $Me_2NCO$ | 1, 9 |
| $C_{10}H_7(\alpha)$ | $n.Pr_2NCO$ | 9 |
| $CONMe_2$ | p-tolyl | 1 |
| trans-p-MeS-styryl | $Et_2NCO$ | 1, 9 |
| Biphenylyl | $Et_2NCO$ | 1, 9 |
| trans-p-NCS-styryl | $Et_2NCO$ | 2 |

Table I-continued

| R⁶ | R⁷ | Rhinovirus Serotype |
|---|---|---|
| trans-p-MeS-styryl | pyrrolidinocarbonyl | 5, 9 |
| " | MeEtNCO | 1B, 9 |
| " | (n-Pr)₂NCO | 1B |

The anti-viral compounds may be formulated for administration in conjunction, if desired, with one or more pharmaceutical or veterinary carriers or excipients suitable, for example for oral, topical, rectal, intravaginal or parenteral administration. The pharmaceutical or veterinary composition so formed may include other therapeutically effective compounds, for example antiinflammatory agents such as steroids, e.g. betamethasone-21-phosphate, or antibiotics such as tetracycline.

5-Diethylcarbamoyl-3α-naphthyl-1,2,4-oxadiazole and 3-biphenylyl-5-diethylcarbamoyl-1,2,4-oxadiazole have been found to be particularly suitable for formulation for topical administration.

Solid preparations for oral consumption are usually presented in unit dose form and include for instance, tablets, capsules, lozenges, chewing gum and medicated sweets.

Each dosage unit preferably contains 0.05 to 4 g of active antiviral material, advantageously 0.1 to 1.0 g. The material may be administered, for example, 1 to 3 times per day but the total daily dose should be in the range 0.1 to 7 g. It will be seen from the forgoing table that the compounds are of particular interest in combatting Rhinovirus infections.

Conventional carriers for such preparations may be sugars, starches, sugar alcohols, gelatin, chicle gum, cocoa butter, etc., together with other compounding agents required such as binders, lubricants, stabilisers, coatings, flavourings and colourings. The compositions may also take the form of liquid oral preparations for ingestion such as solutions, suspensions, syrups, elixirs, emulsions, granules for reconstitution before use, etc., which may contain suspending, emulsifying, stabilising and preserving agents and may also contain acceptable sweetening, flavouring or colouring agents. The compounds may be prepared for local application to the mucous membranes of the nose and throat and may take the form of liquid sprays or powder insufflations, nasal drops or ointments, throat paints, gargles or similar preparations. Topical formulations for the treatment of eyes and ears and external applications may be prepared in oily, aqueous or powdered media in the form of conventional ophthalmic preparations and collyria, skin paints, lotions, creams, ointments, dusting powders, medicated dressings, eye drops and lotions, etc. Aerosol forms of the preparations for local application may also be advantageous. Suppositories and pessaries may contain a conventional base e.g. oil of theobroma, polyglycols, glyco-gelatin bases together with surface active agents if required. The injectable preparations may take the form of aqueous or oily solutions, emulsions, suspensions, or solids for reconstitution before use. Suitable vehicles include, for example, sterile, pyrogen-free water, parenterally acceptable oils, oily esters or other non-aqueous media such as propylene glycol if desired containing suspending, dispersing, stabilising, preserving, solubilising, emulsifying or buffering agents.

As stated above, antiparasitic activity has also been shown in the group of compounds in accordance with the invention, particularly against Entamoeba histolytica. 5-Diethylcarbamoyl-3-p-methylsulphinylstyryl-1,2,4-oxadiazole and 5-piperidinocarbonyl-3-trans-p-methylsulphinylstyryl-1,2,4-oxadiazole have been shown to be highly active against this parasite. Other compounds which have shown activity against this parasite are:

5-dimethylcarbamoyl-3-methyl-1,2,4-oxadiazole;
5-methylcarbamoyl-3-methyl-1,2,4-oxadiazole;
5-diethylcarbamoyl-3-p-methoxyphenyl-1,2,4-oxadiazole;
trans-5-diethylcarbamoyl-3-p-methylthiostyryl-1,2,4-oxadiazole;
5-pyrrolidinocarbonyl-3-trans-p-methylsulphinylstyryl-1,2,4-oxadiazole;
5-n-butylcarbamoyl-3-trans-p-methylsulphinylstyryl-1,2,4-oxadiazole;
5-methylcarbamoyl-3-trans-p-methylsulphinylstyryl-1,2,4-oxadiazole;
5-di-n-propylcarbamoyl-3-trans-p-methylsulphinylstyryl-1,2,4-oxadiazole;
5-ethylcarbamoyl-3-trans-p-methylsulphinylstyryl-1,2,4-oxadiazole;
5-N-ethyl-N-methylcarbamoyl-3-trans-p-methylsulphinylstyryl-1,2,4-oxadiazole;
5-piperidinocarbamoyl-3-trans-p-methylthiostyryl-1,2,4-oxadiazole.

Activity has also been shown against the Helminth Nematospiroides dubius, particularly by 5-dimethylcarbamoyl-3-phenyl-1,2,4-oxadiazole.

Trans-5-diethylcarbamoyl-3-(5-nitrofuryl-2-ylvinyl)-1,2,4-oxadiazole has also shown activity against S. aureus, E. coli, B.C.G. S. typhinurium. It has also been found to be active against M. canis.

The compounds may be formulated for antiparasitic and antibacterial administration by the methods described above. When presented in unit dose form, each dosage unit may generally contain 2–500 mg, preferably 2–250 mg, of the active ingredient. The material may be administered at a daily dose of 0.5 to 100 mg/kg, preferably 1–60 mg/kg, and most conveniently 1–20 mg/kg body weight.

The invention is further illustrated by the following examples. The preparation of certain novel starting materials is given as a series of Preparations. The products of these Preparations are then used in the Examples.

PREPARATION 1

5-Ethoxycarbonyl-3-methyl-1,2,4-oxadiazole

To a stirred suspension of acetamidoxime (3.2g.) in ethanol-free chloroform (25 ml.) containing pyridine (10 ml.) was added ethyl oxalyl chloride (8.7 g.) with cooling. The resulting solution was heated under reflux for one hour and then cooled, shaken with 2-N-hydrochloric acid (30 ml), and then water (25 ml.), dried, and evaporated to dryness to give a yellow oil. Distillation under vacuum gave title compound (4.36 g.) b.p. 57°–61° at 0.4 mm. $\nu_{max}$. (CHBr₃) 1750 cm.⁻¹ (—CO₂Et).

PREPARATION 2

5-Ethoxycarbonyl-3-α-naphthyl-1,2,4-oxadiazole

A solution of ethoxalyl chloride (24 ml.) in ethanol-free chloroform (25 ml.) was added dropwise with cooling during 30 min. to a suspension of α-naphthyl-carbonamidoxime (34.78g.) in ethanol-free chloroform (120 ml.) containing pyridine (30 ml.). The mixture was heated under reflux for 1 hr. and cooled. The solution was washed with 2N-hydrochloric acid and water and then dried. The chloroform solution was evaporated to dryness under reduced pressure leaving a pale yellow solid which was stirred with aqueous methanol to give title compound (31.8 g), m.p. 68°–70°, $\lambda_{max}$. (EtOH) 302 nm ($\epsilon$ 8,420). Similarly was prepared

PREPARATION 3

3-Biphenylyl-5-ethoxycarbonyl-1,2,4-oxadiazole in 98.6% yield, m.p. 81°–82° (MeOH), $\lambda_{max}$. (EtOH) 272 nm ($\epsilon$ 26,400), $\nu_{max}$. (CHBr$_3$) 1750 cm.$^{-1}$ (CO$_2$Et).

PREPARATION 4

5-Ethoxycarbonyl-3-trans-p-methylthiostyryl-1,2,4-oxadiazole

Ethoxalyl chloride (8.7g.) in ethanol-free chloroform (50 ml.) was added during 1 hr. to a stirred suspension of p-methylthiocinnamamidoxime (11.6g.) in chloroform (600 ml.) and pyridine (5.15 ml.) at −3°. After 16 hr. at −20° the solution was filtered and refluxed for 1 hr. with azeotropic removal of water. The solution was cooled and washed successively with 2N-hydrochloric acid, sodium hydrogen carbonate solution and water. The solution was dried and evaporated. The residue was crystallised from aqueous acetone (charcoal) to give the title compound (12.7 g.), m.p. 88°–89°, $\lambda_{max}$. (EtOH) 237, 326 nm ($\epsilon$12,400 and 29,500), $\nu_{max}$. (CHBr$_3$) 1752, 1648 and 973 cm.$^{-1}$.

PREPARATION 5

5-Ethoxycarbonyl-3-p-methoxyphenyl-1,2,4-oxadiazole

Ethoxalyl chloride (11 ml.) in ethanol-free chloroform (5.6 ml.) was added at 0° over a period of 45 min. to a stirred solution of p-methoxybenzamidoxime (13.45g.) in chloroform (73 ml.) containing pyridine (6.5 ml.). Stirring was continued at room temperature for a further 2.5 hr. Chloroform was added and the solution was washed successively with 2N-hydrochloric acid, water, sodium hydrogen carbonate, and water. Evaporation left a residue which was chromatographed on silica (1 kg.) in benzeneethyl acetate (9:1 v/v) to give the oxadiazole as an oil (11.73g.) which slowly crystallised. Recrystallisation from aqueous acetone gave the title compound, m.p. 59°–60°, $\lambda_{max}$. (EtOH) 252 nm ($\epsilon$ 21,200).

PREPARATION 6

3-trans-p-Chlorostyryl-5-ethoxycarbonyl-1,2,4-oxadiazole p-Chlorocinnamamidoxime (anhydrous, 25.74g.) was dissolved in chloroform (300 ml.) containing pyridine (10.34g.). Ethyl oxalyl chloride (16.5g.) in chloroform (15 ml.) was added dropwise, with stirring. Stirring was continued for 1 hr., then the mixture was filtered and the filtrate was evaporated to dryness under reduced pressure. The residue was recrystallised from aqueous ethanol to give title compound (9.76 g.), m.p. 94°–95°. $\lambda_{max}$. (EtOH) 228, 285,nm. ($\epsilon$ 12,990, 31,450) $\nu_{max}$. (CHBr$_3$) 975 cm.$^{-1}$ (trans-CH=CH).

PREPARATION 7

3,5-Bis-ethoxycarbonyl-1,2,4-oxadiazole

Ethyl oxalyl chloride (10 ml.) was added dropwise, with cooling, to a solution of ethoxycarbonyl-formamidoxime (10g.) in ethanol-free chloroform (100 ml.) containing pyridine (10 ml.). The mixture was heated under reflux for 1 hr., cooled and washed with 2N-hydrochloric acid (50 ml.) and water (50 ml.) and dried. Evaporation gave title compound (6.5 g.), $n_D^{21}$ 1.4571.

PREPARATION 8

5-Hydrazinocarbonyl-3-α-naphthyl-1,2,4-oxadiazole

5-Ethoxycarbonyl-3-α-naphthyl-1,2,4-oxadiazole (10.0g.) was dissolved in methanol (150 ml.) and hydrazine hydrate (10.0g.) added dropwise with cooling. The mixture was stirred for fifteen minutes and the crystalline precipitate was filtered off, washed with methanol (10 ml.), and dried to give title compound (7.08 g), m.p. 211°–212° (decomp.) $\lambda_{max}$. (EtOH) 302 nm ($\epsilon$ 10,100) $\nu_{max}$. (Nujol) 1680 cm.$^{-1}$ (—CONH—).

Similarly were prepared

PREPARATION 9

5-Hydrazinocarbonyl-3-methyl-1,2,4-oxadiazole in 54.7% yield, m.p. 150°–151°, $\nu_{max}$. (Nujol) 1672 cm.$^{-1}$ (—CONH—).

PREPARATION 10 trans-5-Hydrazinocarbonyl-3-p-methylthiostyryl-1,2,4-oxadiazole in 92.4% yield, m.p. 207° (decomp.) $\lambda_{max}$. (EtOH) 238, 326 nm. ($\epsilon$ 15,300, 31,000) $\nu_{max}$. (Nujol) 1670 cm.$^{-1}$ (—CONH—) $\tau$ (d$^6$ DMSO) 7.47 (CH$_3$S—) 2.73 (doublet, J 16 Hz.) and 2.24 (doublet, J 16 Hz.) -CH=CH- (trans).

PREPARATION 11

5-Azidocarbonyl-3-α-naphthyl-1,2,4-oxadiazole

5-Hydrazinocarbonyl-3-α-naphthyl-1,2,4-oxadiazole (6.47g.) was dissolved in acetic acid (125 ml.) and 2N-hydrochloric acid (75 ml.). A solution of sodium nitrite (2.0g) in water (6 ml.) as added at 0° with stirring. After 15 minutes the precipitate was filtered off and dissolved in chloroform. The chloroform solution was washed with water and dried (MgSO$_4$). Evaporation to dryness gave title compound (5.82 g.), m.p. 114° (decomp.), $\lambda_{max}$. (EtOH) 300 nm. ($\epsilon$ 8,250), $\nu_{max}$. (CHBr$_3$) 1710 (C=O), 2150 and 2190 cm.$^{-1}$ (N$_3$).

Similarly were prepared

PREPARATION 12 trans-5-Azidocarbonyl-3-p-methylthiostyryl-1,2,4-oxadiazole in 73.7% yield, m.p. 125° (decomp.) $\lambda_{max}$. (EtOH) 237, 325 nm. ($\epsilon$ 12,400, 24,300), $\nu_{max}$. (CHBr$_3$) 1715 (C=O), 2160 and 2202 cm.$^{-1}$ (N$_3$), $\tau$ (d$_6$-DMSO) values include 2.21 (doublet J 16 Hz) and 2.68 (doublet J 16 Hz, trans CH=CH).

PREPARATION 13

5-Azidocarbonyl-3-methyl-1,2,4-oxadiazole in 33.4% yield, m.p. 71°–72°, $\nu_{max}$. (CHBr$_3$) 1710 (C=O), 2150 and 2192 cm.$^{-1}$ (N$_3$).

PREPARATION 14

3-Ethoxycarbonyl-5-p-tolyl-1,2,4-oxadiazole

Ethoxycarbonylformamidoxime (46.0g.) was stirred in chloroform (450 ml.) and pyridine (32.5 ml.) and a solution of p-tolyl chloride (54g.) in chloroform (50 ml.) was added during 1 hr. and stirring was continued for a further 1 hr. The solid that separated was filtered off and washed with water to give the O-acylated amidoxime (63.5g., 72%), m.p. 188°–190°. Part of this product (5.0g.) was heated under reflux in xylene (100 ml.) for 4 hr. with azeotropic removal of water; the xylene was then removed under reduced pressure. The residue was recrystallised from aqueous methanol to give the title compound (4.4g.), m.p. 76°–77°, $\lambda_{max}$. (EtOH) 263 nm. ($\epsilon$ 19,620) $\nu_{max}$. (CHBr$_3$) 1750, 1210 cm.$^{-1}$ (CO$_2$Et).

PREPARATION 15

5-p-Chlorophenyl-3-ethoxycarbonyl-1,2,4-oxadiazole p-Chlorobenzoyl chloride (9.5g.) in chloroform (20 ml.) was added dropwise to a stirred solution of ethoxycarbonylformamidoxime (7.21g.) in chloroform (60 ml.) and pyridine (18 ml.). After 1 hr. the solid (12.32g.) was filtered off and washed with chloroform. Some of this solid (10.0 g.) was heated under reflux in xylene (250 ml.) for 20 hr., with azeotropic removal of water. The xylene was removed under reduced pressure, and the residue was recrystallised from ethanol to give title compound (8.11 g.), m.p. 93.5°, $\lambda_{max}$. (EtOH) 261–262 nm. ($\epsilon$ 2,540), $\nu_{max}$. (CHBr$_3$) 1745 and 1210 cm.$^{-1}$ (CO$_2$Et). The following compounds were similarly prepared:

PREPARATION 16

3-Ethoxycarbonyl-5-p-nitrophenyl-1,2,4-oxadiazole in 88% yield, m.p. 144°–145°, $\lambda_{max}$.$^{(EtOH)}$274 nm ($\epsilon$ 21,200) $\nu_{max}$. (CHBr$_3$)1750 and 1218 (CO$_2$Et), 1536 and 1350 cm.$^{-1}$ (NO$_2$).

PREPARATION 17

3-Ethoxycarbonyl-5-(2-thienyl)-1,2,4-oxadiazole in 43% yield, m.p. 76°, $\lambda_{max}$.$^{(EtOH)}$263–264, 289 nm, ($\epsilon$10,960, 16,280), $\nu_{max}$. (CHBr$_3$) 1210 and 1745 cm.$^{-1}$ (CO$_2$Et).

PREPARATION 18

3-Ethoxycarbonyl-1,2,4-oxadiazole

Ethoxycarbonylformamidoxime (39.6g., 300 mmole) was added to triethyl orthoformate (180 ml.) containing boron trifluoride etherate (0.9 ml.), and the solution was heated under reflux for 1 hr., then cooled and filtered. The filtrate was evaporated to dryness under reduced pressure and the residue, dissolved in chloroform was washed with 2N-hydrochloric acid, then with saturated sodium hydrogen carbonate solution and dried (MgSO$_4$). Removal of the solvent left an oil (37.2g.) which partially crystallised. The residual oil was sucked off, leaving the oxadiazole, (33.94g), m.p. 41°–43°, b.p. 80°–90° (bath)/0.6 mm.

PREPARATION 19

3-Hydrazidocarbonyl-1,2,4-oxadiazole

Hydrazine hydrate (98%, 3.15 ml.) was added at <15° in 3 portions during 20 min. to a stirred solution of 3-ethoxycarbonyl-1,2,4-oxadiazole (5.96 g.) in dry ethanol (29 ml.). The mixture was stirred for 50 min. at 0° and then filtered, to give title compound 5.26 g., m.p. 112° (decomp.) $\lambda_{max}$. 242–243 nm ($\epsilon$ 3,950).

PREPARATION 20

3-Azidocarbonyl-1,2,4-oxadiazole

Sodium nitrite (2.70g.) in water (7.5 ml.) was added, at 0°, with stirring, during 40 min., to a solution of 3-hydrazidocarbonyl-1,2,4-oxadiazole (4.48 g.) in 2N-hydrochloric acid (50 ml.) and glacial acetic acid (20 ml.). After 1 hr., water was added and the product was extracted into chloroform Evaporation of the solvent and removal of residual acetic acid under vacuum gave the azide, (3.17 g), m.p. 89°–90°, $\lambda_{max}$. (EtOH) 241 nm ($\epsilon$ 4,580).

PREPARATION 21

3-Chlorocarbonyl-1,2,4-oxadiazole

Dry hydrogen chloride was passed for 2 hr. through a solution of 3-hydrazidocarbonyl-1,2,4-oxadiazole (11.96g., 93.7 mmole) in dry methanol (630 ml.), then the solution was evaporated to dryness. Dry nitromethane (30 ml.) was added and the evaporation was repeated. The residue was dissolved in nitromethane (200 ml.) and hydrogen chloride was again passed into the solution for 45 min. Chlorine was then passed in for 1 hr., when the evolution of nitrogen ceased. The residual chlorine was removed by the passage of nitrogen, the suspension was filtered, and the filtrate was evaporated to give the crude acid chloride, 10.2 g. Distillation gave title compound b.p. 47–47.5°/2.5 mm. $\nu_{max}$. (CS$_2$) 1785 (COCl), 3130 cm.$^{-1}$ (CH).

PREPARATION 22

5-Ethoxycarbonyl-3-$\alpha$-naphthyl-1,2,4-oxadiazole $\alpha$-Naphthylcarbonamidoxime (149.5 g.) was suspended in dry ethyl acetate (510 ml.) and propylene oxide (153 ml.). A solution of ethyl oxalyl chloride (97 ml.) in dry ethyl acetate (100 ml.) was added to the stirred suspension at 0° to 5° during 1 hour. The solution was stirred at room temperature for 30 minutes and then heated under reflux for 2 hours. The cooled solution was washed with 2N-sodium carbonate solution and water and dried over sodium sulphate. Removal of the solvent under reduced pressure gave a brown oil (237.9 g.) which was vigorously stirred with methanol-water (7:1, v/v) (131 ml.), and dried to give the ester (193.1 g., 89.7%), m.p. 72°–73°.

PREPARATION 23

5-Ethoxycarbonyl-3-p-methoxystyryl-1,2,4-oxadiazole p-Methoxycinnamamidoxime (1.25 g.) was stirred in dry ethyl acetate (20 ml.) and propylene oxide (0.9 ml.) was added. A solution of ethyl oxalyl chloride (0.84 ml.) in ethyl acetate (5 ml.) was added dropwise, with stirring, during 30 minutes at 0°–5°. The suspension was allowed to warm to 18° and was then heated under reflux for 90 minutes. The solution was cooled, washed with 2N-sodium carbonate solution and with water, dried and treated with charcoal. Removal of the solvent and recrystallisation from methanol gave the oxadiazole (1.534 g., 86%), m.p. 115°–116°, $\lambda_{max}$. (EtOH) 225.5, 300 (infl.), and 308.5 nm ($\epsilon$ 14500, 26000 and 26600), $\nu_{max}$. (CHBr$_3$) 820 (C$_6$H$_4$) 970 (trans-CH=CH), 1752 (C=O), cm.$^{-1}$.

PREPARATION 24 trans-5-Ethoxycarbonyl-3-(5-nitrofur-2-ylvinyl)-1,2,4-oxadiazole trans-5-Nitrofur-2-ylacrylamidoxime (2.0 g.) was suspended in ethanol-free chloroform (40 ml.) containing pyridine (1.6 ml.). Ethoxalyl chloride (2.5 ml.) was added dropwise and the mixture was heated under reflux for 2 hours. After cooling the reaction mixture was poured into water (100 ml.) and extracted with chloroform (100 ml.). The dried (MgSO4) extract was evaporated to dryness and the residue was crystallised from methanol (90 ml.) to give the title compound (2.3 g., 80%), m.p. 138°–139°, $\nu_{max.}$ (CHBr$_3$) 1755 (CO$_2$Et), 1508 and 1350 (NO$_2$), 959 cm.$^{-1}$ (trans CH=CH).

PREPARATION 25

3-Benzyl-5-ethoxycarbonyl-1,2,4-oxadiazole

Ethoxalyl chloride (1.75 ml.) in dry ethylacetate (10 ml.) was added at 0°–5° during 10 minutes to a stirred solution of phenylacetamidoxime (1.5 g.) in ethylacetate (10 ml.). After stirring at room temperature for 90 minutes the mixture was heated under reflux for 2½ hours. The solution was washed with 2N-sodium carbonate and water, dried and evaporated to give a yellow oil which was chromatographed on silica (100 g.). Elution with benzene/ethylacetate (3:1) gave the oxadiazole (2.25 g.) which was subsequently distilled, b.p. 170°–180° at 1.3 mm $\nu_{max.}$ (CHBr$_3$) 1750 cm$^{116\ 1}$ (ester).

EXAMPLE 1

5-Diethylcarbamoyl-3-α-naphthyl-1,2,4-oxadiazole.

5-Ethoxycarbonyl-3-α-naphthyl-1,2,4-oxadiazole (30.9 g.) was heated under reflux in an excess of diethylamine (35.6g.) for 1.5 hr. The mixture was cooled and evaporated under reduced pressure to give a solid which was recrystallised from methanol yielding title compound (29.3 g.), m.p. 101.5°–102.5°, $\lambda_{max.}$ (EtOH) 302 nm. (ε 9,700), $\nu_{max.}$ (CHBr$_3$) 1662 cm.$^{-1}$ (CONEt$_2$).

EXAMPLE 2 trans-5-Diethylcarbamoyl-3-p-methylthiostyryl-1,2,4-oxadiazole trans-5-Ethoxycarbonyl-3-p-methylthiostyryl-1,2,4-oxadiazole (600 mg.) was heated to reflux for 30 min. in an ethanolic solution of dimethylamine (10 ml.). The reaction mixture was evaporated to dryness and the solid residue was recrystallised from methanol (8 ml.) to give title compound (544 mg.), m.p. 119°–120°, $\lambda_{max.}$ (EtOH) 238, 315 (inflection), 327 nm. (ε 15,800; 26,000, 30,950) $\nu_{max.}$ (CHBr$_3$) 1668 (—CONMe$_2$) and 978 cm.$^{-1}$(trans CH=CH).

EXAMPLE 3 trans-5-Diethylcarbamoyl-3-p-methylthiostyryl-1,2,4-oxadiazole trans-5-Ethoxycarbonyl-3-p-methylthiostyryl-1,2,4-oxadiazole (13.3g.) was heated under reflux with a mixture of diethylamine (80 ml.) and methanol (20 ml.) for 1 hr. The cooled reaction mixture was evaporated and the residue was recrystallised from aqueous methanol to give the title amide (11.5 g.), m.p. 78°–79°, $\lambda_{max.}^{(EtOH)}$ 237, 311 (inflection), 326 nm (ε 16,100; 23,000, 32,000) $\nu_{max.}$ (CHBr$_3$) 1663 (CONEt$_2$) and 972 cm.$^{-1}$ (trans CH=CH).

EXAMPLE 4

5-Dimethylcarbamoyl-3-α-naphthyl-1,2,4-oxadiazole

5-Ethoxycarbonyl-3-α-naphthyl-1,2,4-oxadiazole (618 mg.) was dissolved in an ethanolic solution of dimethylamine (10 ml., 33% v/v). After 1 hr. The solution was evaporated leaving a residue that was recrystallised from methanol (3.5 ml.) to give title compound (424 mg.,) m.p. 109°–110°, $\lambda_{max.}$ (EtOH) 302.5 nm (ε 9,400) $\nu_{max.}$ (CHBr$_3$) 1660 cm.$^{-1}$ (CONMe$_2$).

EXAMPLE 5

3-Adamant-1-ylcarbamoyl-1,2,4-oxadiazole.

3-Azidocarbonyl-1,2,4-oxadiazole (350 mg.) was added to a solution of 1-aminoadamantane (378 mg.) in chloroform (15 ml.) and the mixture was stirred for 24 hr. The chloroform solution was evaporated to dryness under reduced pressure and the residue was recrystallised from aqueous methanol to give title compound (167 mg.), m.p. 141°–142°, $\nu_{max.}$ (EtOH) 230 nm (ε 3,910), $\lambda_{max.}$ (Nujol) 3392 (—NH—) 1692 and 1515 cm.$^{-1}$ (CONH). Further examples provided in Table II were prepared by the following general methods:

Method A

The appropriate 3- or 5-alkoxycarbonyl-1,2,4-oxadiazole was treated with an excess of the primary or secondary amine (1–10 equivs.) at a suitable temperature, between room temperature and the boiling point. Excess amine was removed under reduced pressure and the product was recrystallised.

Method B

Similar to Method A except that a solvent such as ethanol or methanol was used as diluent.

Method C

The appropriate 3- or 5-azidocarbonyl-1,2,4-oxadiazole was treated with the primary or secondary amine (1–2 equivs.) at room temperature in a suitable solvent (e.g. chloroform) and the product isolated by evaporation and recrystallisation.

Method D

Similar to Method C except that the 3- aor 5-chlorocarbonyl-1,2,4-oxadiazole was used to acylate the amine.

Examples 6–40 and 52–60 refer to the formula

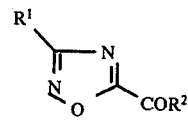

Examples 41–51 refer to the formula

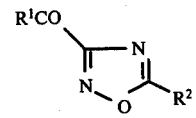

Table II

| Ex. No. | R¹ | R² | Method | Cryst. Solvent | M.p. °C | λ max. nm. (EtOH) | ε | νmax. (—CON<) cm.⁻¹ (CHBr₃) | Yield % |
|---|---|---|---|---|---|---|---|---|---|
| 6 | Ph | —N(CH₃)₂ | B (EtOH) | MeOH | 79–81° | 244 | 7,300 | 1678 (CS₂) | 67 |
| 7 | Ph | —NHCH₃ | B (EtOH) | MeOH | 114–115 | — | — | 1715 (CS₂) | 56 |
| 8 | Ph | —N(C₂H₅)₂ | A | petrol (40–60°) | 45–46 | — | — | 1660 | 71 |
| 9 | Ph | —NHC₂H₅ | A | EtOH/petrol (40–60°) | 89–90 | — | — | 1700 | 79 |
| 10 | CH₃ | —N(CH₃)₂ | B (MeOH) | MeOH/petrol (60–80°) | 35–37 | — | — | 1660 | 70 |
| 11 | Ph | —NHPh | C | MeOH/petrol (80–100°) | 110–112 | — | — | 1710 | 72 |
| 12 | Ph | —N(CH₃)Ph | C | ″ | 83–85 | — | — | 1662 | 63 |
| 13 | CH₃ | —NHCH₃ | B (MeOH) | benzene | 99–101 | — | — | 1658 | 48 |
| 14 | Ph | —N(pyrrolidinyl) | A | EtOH | 138–140 | 231 | 18,000 | 1650 | 60 |
| 15 | Ph | —N(piperidinyl) | A | EtOH | 66–67.5 | 235 | 17,000 | 1660 | 47 |
| 16 | Ph | —N(N-methylpiperazinyl) | A | Et₂O | 81–83 | 224 | 18,300 | 1655 | 49 |
| 17 | Ph | —N(morpholinyl) | A | EtOH | 82–83 | 235 | 15,300 | 1658 | 82 |
| 18 | CH₃O-C₆H₄- | —N(C₂H₅)₂ | A | EtOH | 62–63 | 256.5 | 19,360 | 1643 | 35 |
| 19 | CH₃O-C₆H₄- | —N(piperidinyl) | A | MeOH/H₂O | 78–79 | 258 | 19,660 | 1656 | 43 |
| 20 | CH₃O-C₆H₄- | —N(CH₃)₂ | B (EtOH) | EtOH | 123–124 | 256 | 19,600 | 1665 | 81 |
| 21 | α—C₁₀H₇ | —N(piperidinyl) | A | MeOH/H₂O | 107–108 | 302.5 | 10,260 | 1655 | 55 |
| 22 | α—C₁₀H₇ | —N(CH₃)₂ | B (EtOH) | MeOH | 109–110 | 302.5 | 9,370 | 1660 | 68 |
| 23 | α—C₁₀H₇ | —N(C₃H₇)₂ | A | MeOH | 41.5–43 | 302.5 | 10,350 | 1658 | 52 |
| 24 | α—C₁₀H₇ | —N(CH₃)Ph | C | MeOH | 88–89 | 293 | 8,900 | 1670 | 40 |
| 25 | α—C₁₀H₇ | —N(C₄H₉)₂ | C | — | oil | 302 | 7,450 | 1650 | 78 |
| 26 | (C₂H₅)₂NCO— | —N(C₂H₅)₂ | A | MeOH | 55–56 | 235 inf. | 6,030 | 1660 | 55 |
| 27 | Ph-C₆H₄- | —N(C₂H₅)₂ | A | MeOH | 81–82 | 275.5 | 28,100 | 1660 | 72 |
| 28 | CH₃S-C₆H₄- | —NH-adamantyl | C | EtOH | 130–131 | (238 (327 | 16,800) 30,600) | 1700 | 71.5 |

Table II-continued

| Ex. No. | R¹ | R² | Method | Cryst. Solvent | M.p. °C | λ max. nm. (EtOH) | ε | νmax. (—CON<) cm.⁻¹ (CHBr₃) | Yield % |
|---|---|---|---|---|---|---|---|---|---|
| 29 | α—C₁₀H₇ | —NH-(adamantyl) | C | MeOH/H₂O | 64–65 | 302 | 8,590 | 1696 | 81 |
| 30 | CH₃S—C₆H₄—CH=CH— | —NHC₄H₉ | A | MeOH | 105–106 | (237 (326 | 17,300) 30,500) | 1692 | 57 |
| 31 | Cl—C₆H₄—CH=CH— | —N(C₂H₅)₂ | A | MeOH | 73–74 | (221 (227 (285 | 18,700) 16,100) 31,900 | 1660 | 87 |
| 32 | Cl—C₆H₄—CH=CH— | —N(piperidyl) | A | MeOH | 115–116 | (220 (227.5 | 18,900) 15,400) | 1660 | 80 |
| 33 | CH₃ | —NH-(adamantyl) | C | — | 86–88 | 234 | 6,110 | 1700 | 65 |
| 34 | α—C₁₀H₇ | —N-(bicyclic) | C | MeOH | 120–121 | 302 | 9,480 | 1662 | 59 |
| 35 | CH₃—S—C₆H₄—CH=CH— | —NHC(CH₃)₃ | A | MeOH | 113–114 | (235.5 (325 | 16,800) 30,400) | 1702 | 67 |
| 36 | α—C₁₀H₇—CH=CH— | —N(C₂H₅)₂ | A | MeOH | 84–85 | (226 (246 (322 | 38,900) 25,500) 15,300 | 1665 | 67 |
| 37 | α—C₁₀H₇ | —N(CH₂CH₂OH)₂ | B | MeOH | 118–119 | 301.5 | 9,300 | 1662 | 66 |
| 38 | αC₁₀H₇ | —NH-(cyclohexyl) | B | MeOH | 119–120 | 302.5 | 8810 | 1695 | 75 |
| 39 | αC₁₀H₇ | —NHCH₂CH=CH₂ | B | EtOH | 105–106 | 302.5 | 8700 | 1700 | 74 |
| 40 | PhCH—₂ | —N(C₂H₅)₂ | A | — | Oil | 253.5 | 2200 | 1662 | 100 |
| 41 | (CH₃)₂N— | CH₃ | B (MeOH) | — | liquid | — | — | 1660 | 48 |
| 42 | CH₃NH— | CH₃ | B (MeOH) | MeOH/petrol (40–60°) | 109–110 | — | — | 1700 | 74 |
| 43 | (CH₃)₂N— | Ph | C | CHCl₃/petrol 60–80° | 80–81 | — | — | 1658 | 78 |
| 44 | (C₂H₅)₂N— | Ph | A | — | liquid | — | — | 1640 | 68 |
| 45 | Cl—C₆H₄—NH— | H | C,D | — | 156–157 | 271.5 | 11,300 | 1710 | 77, 97 |
| 46 | (CH₃)₂N— | Cl—C₆H₄— | B (MeOH) | MeOH/H₂O | 97–99 | 260 | 28,200 | 1650 | 65 |
| 47 | (CH₃)₂N— | α—C₁₀H₇ | B (MeOH) | MeOH/H₂O | 109–110 | 239) 312) | 27,600 1700 | 1652 | 70 |
| 48 | (CH₃)₂N— | (methylthienyl) | B (MeOH) | MeOH/H₂O | 113–114 | 287 | 17,500 | 1650 | 72 |
| 49 | (C₂H₅)₂N— | O₂N—C₆H₄— | B (CHCl₃) | MeOH/H₂O | 119–120 | 274 | 19,400 | 1645 | 35 |

Table II-continued

| Ex. No. | R¹ | R² | Method | Cryst. Solvent | M.p. °C | $\lambda$ max. nm. (EtOH) | $\epsilon$ | $\nu$max. (—CON<) cm.⁻¹ (CHBr₃) | Yield % |
|---|---|---|---|---|---|---|---|---|---|
| 50 | (CH₃)₂N— | CH₃-C₆H₄- (p-tolyl) | B | MeOH (MeOH) | 58–59 | 262 | 30,900 | 1660 | 58 |
| 51 | bicyclic amine-N— | H | C | MeOH/H₂O | 128–129 | — | — | 1650 | 73 |
| 52 | CH₃S-C₆H₄-CH=CH- | —N(aziridine) | B | aqueous methanol | 117–118 | 237.5 327 | 17,000 30,000 | 1650 | 87 |
| 53 | " | —N(piperidine) | B | ethanol | 137–139 | 237 326.5 | 15,900 30,600 | 1660 | 93 |
| 54 | " | —N(morpholine) | B | methanol | 122–123 | 236.5 326.5 | 16,300 30,000 | 1660 | 93 |
| 55 | " | —N(N-methylpiperazine)NCH₃ | B | aqueous acetone | Ca. 45 | 236.5 327 | 16,500 29,900 | 1660 | 85 |
| 56 | " | —NH CH₃ | B | ethanol | 200–202 | 235 326 | 16,800 29,200 | 1708 | 84 |
| 57 | " | —NHC₂H₅ | B | aqueous methanol | 123–124 | 236 326 | 17,500 28,900 | 1704 | 87 |
| 58 | " | —N(CH₃)C₂H₅ | B | methanol | 74–76 | 236 326 | 15,600 30,000 | 1665 | 77 |
| 59 | " | —N[C₃H₇(n)]₂ | B | methanol | 58–59 | 237 326 | 16000 32,000 | 1652 | 56 |
| 60 | " | —NHC₄H₉(n) | B | aqueous methanol | 110–111 | 236 326 | 17,200 29,200 | 1700 | 96 |

EXAMPLE 61

5-Diethylcarbamoyl-3-trans-p-methylsulphinylstyryl-1,2,4-oxadiazole.

Peracetic acid (1 ml., comml. ca. 40%) was extracted with methylene chloride (5 ml.) and a portion (3.5 ml.) of this extract was added dropwise at room temperature to a stirred solution of 5-diethylcarbamoyl-3-trans-p-methylthiostyryl-1,2,4-oxadiazole (1.00g) in methylene chloride (50 ml.) during 70 minutes. The solution was shaken with saturated sodium hydrogen carbonate solution (20 ml), and then water (20 ml), and dried Removal of the solvent reduced pressure gave an off-white solid which was stirred with petroleum (50 ml, b.p. 40°–60°), filtered off and dried under vacuum to give title compound (1.00 g.), m.p. 101.5°–102°, $\lambda_{max}$. (EtOH) 288.5 nm ($\epsilon$ 32,000), $\nu_{max}$. (CHBr₃) 1650 (CONEt₂) and 970 cm.⁻¹ (trans CH=CH), $\tau$ (CDCl₃) values include 2.19, 2.82 (quartet J 16.5 Hz, trans CH=CH) and 7.25 (SOMe).

EXAMPLE 62

5-Diethylcarbamoyl-3-trans-p-methylsulphonylstyryl-1,2,4-oxadiazole

Peracetic acid (3 ml. comml. ca. 40%) was extracted with methylene chloride (15 ml) and a portion (9.0 ml) of this extract was added dropwise at room temperature to a stirred solution of 5-diethylcarbamoyl-3-trans-p-methylthiostyryl-1,2,4-oxadiazole (0.961g.) in methylene chloride (50 ml.) during 100 minutes. The solution was shaken with saturated sodium hydrogen carbonate solution (30 ml), and then water (20 ml), and dried Removal of the solvent under reduced pressure gave title compound (1.01 g.), m.p. 123°–124°, $\lambda_{max}$. (EtOH) 284.5nm ($\epsilon$34,900), $\nu_{max}$. (CHBr₃) 1650 (CONEt₂) and 952 cm.⁻¹ (trans CH=CH), $\tau$ (CDCl₃) values include 2.17, 2.77 (quartet J 16.5, Hz, trans CH=CH) and 6.90 (SO₂Me).

EXAMPLE 63

5-Dimethylcarbamoyl-3-p-methylsulphinylstyryl-1,2,4-oxadiazole

5-Dimethylcarbamoyl-3-p-methylthiostyryl-1,2,4-oxadiazole (700 mg.) was dissolved in methylene chloride (40 ml.). A solution of ca. 40% peracetic acid in methylene chloride (6.7% w/v; 2.8 ml.) was added dropwise at room temperature; the reaction was followed by thin-layer chromatography. The solvent was removed under reduced pressure and the residual solid was stirred with light petroleum (b.p. 40°–60°), leaving the sulphoxide (670 mg., 90.7%), m.p. 136°–137°. A sample recrystallised from toluene had m.p. 137°–138°, $\lambda_{max}$. (EtOH) 226, 288.5, and 305 nm, ($\epsilon$13900, 33200, and 21500) $\nu_{max}$. (CHBr₃) 317 (C₆H₄). 972 (trans-CH=CH), 1043 (S → 0), 1660 cm⁻¹ (CON<).

EXAMPLE 64

5-Diethylcarbamoyl-3-p-methoxystyryl-1,2,4-oxadiazole

5-Ethoxycarbonyl-3-p-methoxystyryl-1,2,4-oxadiazole (1.25 g.) was suspended in dry methanol (5 ml.) and diethylamine (7.25 ml.) was added. The mixture was heated under reflux for 1 hour, when a solution was obtained. The solvent was removed under reduced pressure and the residual oil was dissolved in methanol and treated with charcoal. Evaporation of the filtrate left an oil, which was recrystallised from aqueous methanol to give the amide (1.199 g., 87.4%), m.p. 69°–70°, $\lambda_{max}$. (EtOH) 225.5 300 (infl.) and 308 nm. ($\epsilon$15400, 24400 and 25000), $\epsilon_{max}$. (CHBr$_3$) 820 (C$_6$H$_4$), 970 (trans-CH=CH), 1650 (CO.N<),

EXAMPLE 65 trans-5-Diethylcarbamoyl-3-(5-nitrofur-2-ylvinyl)-1,2,4-oxadiazole trans-5-Ethoxycarbonyl-3-(5-nitrofur-2-ylvinyl)-1,2,4-oxadiazole (332 mg.) was heated under reflux with diethylamine (5 ml.) for 30 min. to give a deep red solution. Evaporation gave a red solid; recrystallisation from methanol (3 ml.) gave trans-5-diethylcarbamoyl-3-(5-nitrofur-2-ylvinyl)1,2,4-oxadiazole (208 mg., 57%), m.p. 118°–119°, $\lambda_{max}$. (EtOH) 240 and 349 nm. ($\epsilon$18,600 and 19,900), $\nu_{max}$. (CHBr$_3$) 1665 (CONEt$_2$), 1510, 1352 (NO$_2$) and 960 cm.$^{-1}$ (trans CH=CH).

EXAMPLE 66

The following compounds were prepared as described in Example 63.

3-trans-p-methylsulphinylstyryl-5-pyrrolidinocarbonyl-1,2,4-oxadiazole

74% yield, m.p. 162°–163° (from toluene-light petroleum b.p. 80°–100°), $\lambda_{max}$ (EtOH) 289.5 and 305 nm ($\epsilon$31,900 and 21,400), $\nu_{max}$. (CHBr$_3$) 812 (p-C$_6$H$_4$), 970 (trans-CH=CH), 1041 (S → O), 1655 cm$^{-1}$ (CON<).

3-trans-p-methylsulphinylstyryl-5-piperidinocarbonyl-1,2,4-oxadiazole

73% yield, m.p. 95°–96° (from toluene-light petroleum, b.p. 80°–100°), $\lambda_{max}$. (EtOH) 288.5 nm ($\epsilon$21,200), $\nu_{max}$. (CHBr$_3$) 812 (p-C$_6$H$_4$), 9701 (trans-CH=CH), 1041 (S → O), 1660 cm$^{-1}$ (CON<).

5-Methylcarbamoyl-3-trans-p-methylsulphinylstyryl-1,2,4-oxadiazole

76% yield, m.p. 193°–194° (from toluene-ethanol), $\lambda_{max}$. (EtOH) 288.5 nm ($\epsilon$ 31,600), $\nu_{max}$. (Nujol) 818 (p-C$_6$H$_4$), 969 (trans-CH=CH), 1030 (S → O), 1680 cm$^{-1}$ (CONH).

5-Ethylcarbamoyl-3-trans-p-methylsulphinylstyryl-1,2,4-oxadiazole

73% yield, m.p. 147°–148° (from toluene-ethanol), $\lambda_{max}$. (EtOH) 288 nm ($\epsilon$ 32,800), $\nu_{max}$. (CHBr$_3$) 811 (p-C$_6$H$_4$), 970 (trans-CH=CH), 1040 (S → O), 1648 cm$^{-1}$ (CONH).

5n-Butylcarbamoyl-3-trans-p-methylsulphinylstyryl-1,2,4-oxadiazole

83% yield, m.p. 130°–131° (from toluene-light petroleum, b.p. 80°–100°), $\lambda_{max}$ (EtOH) 288.5 nm ($\epsilon$ 32,300), $\nu_{max}$. (CHBr$_3$) 812 (p-C$_6$H$_4$), 970 (trans-(CH=CH), 1040 (S → O), 1624 cm$^{-1}$ (CONH).

5-N-Ethyl-N-methylcarbamoyl-3-trans-p-methylsulphinylstyryl-1,2,4-oxadiazole 86.5% yield, m.p. 109° (from toluene), $\lambda_{max}$. (EtOH) 288.5 nm ($\epsilon$ 34,500) $\nu_{max}$. (CHBr$_3$) 820 (p-C$_6$H$_4$), 978 (trans-CH=CH), 1050 (S → O), 1670 cm$^{-1}$ (CON<).

3-trans-p-Methylsulphinylstyryl-5-di-n-propylcarbamoyl-1,2,4-oxadiazole.

66% yield, liquid (from aqueous methanol), $\lambda_{max}$. (EtOH) 289 nm ($\epsilon$ 28,200), $\nu_{max}$. (CHBr$_3$) 818 (p-C$_6$H$_4$), 977 (trans-CH=CH), 1050 (S → O), 1670 cm$^{-1}$ (CON<).

EXAMPLE 67

5-Diethylcarbamoyl-3-trans-p-thiocyanatostyryl-1,2,4-oxadiazole 3-trans-p-Aminostyryl-5-diethylcarbamoyl-1,2,4-oxadiazole (1.42 g) was dissolved in glacial acetic acid (30 ml) and 2N-sulphuric acid (10 ml). The solution was stirred, and sodium nitrite (400 mg) in water (10 ml) was slowly added at <5°. The diazonium solution was added dropwise at 0° to a stirred aqueous solution of cuprous thiocyanate (1.5 g) and potassium thiocyanate (15 g). The mixture was allowed to warm to room temperature and the pH was adjusted to 7 (NaHCO$_3$). The solid that separated was extracted into chloroform. The filtered chloroform solution was washed with sodium hydrogen carbonate solution and with water, dried (Na$_2$SO$_4$) and evaporated, leaving an oil, which slowly crystallised. The crystals were washed with a little methanol, giving the thiocyanate compound (700 mg, 43%), m.p. 97°, $\lambda_{max}$. (EtOH) 291.5 nm ($\nu$ 29,000), 223 nm ($\epsilon$ 15,400) $\nu_{max}$. (CHBr$_3$) 1662 (—CON<), 972 (trans-CH=CH), 814 (p-C$_6$H$_4$), 2180 cm$^{-1}$ (SCN).

The starting material for the above transformation was prepared from p-nitrocinnamamidoxime by the following sequence 5-Ethoxycarbonyl-3-trans-p-nitrostyryl-1,2,4-oxadiazole.

p-Nitrocinnamamidoxime (17.06 g) was stirred in ethyl acetate (1 l) containing propylene oxide (8.8 ml, 9.63 g). Ethyl oxalyl chloride (16.9 ml, 13.6 g) was added dropwise during 45 min. The solution was refluxed for 1.5 hr, cooled, and washed with 2N-sodium carbonate, then with water, dried (Na$_2$SO$_4$), and treated with charcoal. The filtered solution was evaporated under reduced pressure and the residue was recrystallised from toluene to give the ester (14.02 g; 59%), m.p. 145°, $\lambda_{max}$. (EtOH) 308.5nm ($\epsilon$ 22,800), $\lambda_{infl}$. 228 nm ($\epsilon$ 11,800), $\nu_{max}$. (CHBr$_3$) 1525 and 1348 (NO$_2$), 1753 (CO$_2$Et), 835 (p-C$_6$H$_4$), 972 cm$^{-1}$ (trans-CH=CH).

5-Diethylcarbamoyl-3-trans-p-nitrostyryl-1,2,4-oxadiazole

5-Ethoxycarbamoyl-3-trans-p-nitrostyryl-1,2,4-oxadiazole (13.0 g) was refluxed in diethylamine (102 ml, 72.4 g) dissolved in methanol (520 ml) and ethanol (200 ml) for 1.5 hr. The solution was treated with charcoal, filtered, and evaporated. The residue was recrystallised from aqueous methanol to give the amide (11.7 g, 82.5%), m.p. 118°, $\lambda_{max}$. (EtOH) 305.5 nm ($\epsilon$ 26,100), $\lambda_{infl}$. 234.5 nm ($\epsilon$ 12,700) $\nu_{max}$. (CHBr$_3$) 1529 and 1349 (NO$_2$), 1666 (—CON<), 838 (p-C$_6$H$_4$), 974 cm$^{-1}$ (trans-CH=CH).

3-trans-p-Aminostyryl-5-diethylcarbamoyl-1,2,4-oxadiazole

5-Diethylcarbamoyl-3-trans-p-nitrostyryl-1,2,4-oxadiazole (11.2 g) was dissolved in acetone (250 ml) and acid titanous chloride solution (15% W/V; 260 ml) was added to the stirred solution during 1 hr. The pH was adjusted to 7 and the solid that separated was filtered off and dissolved in acetone. The acetone solution was filtered and evaporated, leaving the crude amine (10.7 g,>100%), m.p. 174°–180°, $\nu_{max}$. (Nujol) 3435-3130 (bonded NH$_2$), 1645 (—CON<), 812 (p-C$_6$H$_4$, 962 cm$^{-1}$ (trans-CH=CH), $\tau$ (Me$_2$SO d6) 4.36 (NH$_2$).

EXAMPLE 68

| Tablet | |
|---|---|
| 3-α-naphthyl-5-diethylcarbamoyl-1,2,4-oxadiazole | 500 mg |
| Lactose | 60 mg |
| Gum Acacia | 30 mg |
| Magnesium stearate | 10 mg |

The active ingredient was taken up in sufficient water to form a granulating fluid and the pH value adjusted to about 5.0 with the aid of citric acid. The gum acacia was dissolved in the same solution and this solution was used to granulate the lactose. The granules were passed through a 20 mesh (B.S.) sieve, dried, lubricated with the magnesium stearate and compressed.

EXAMPLE 69

Tablet

Tablets were prepared as described in Example 51 using half quantities of excipients and 250 mg. per tablet of 3-p-methylthiostyryl-5-diethylcarbamoyl-1,2,4-oxadiazole as active ingredient.

EXAMPLE 70

| Hard gelatin capsules | |
|---|---|
| 3-α-naphthyl-5-diethylcarbamoyl-1,2,4-oxadiazole | 250 mg |
| Lactose | 47 mg |
| Magnesium stearate | 3 mg |

The active ingredient and the lactose were blended together homogeneously. The magnesium stearate was also blended in to provide good flow properties and the powder distributed into hard gelatin capsules so that each contained 250 mg. of the active ingredient.

EXAMPLE 71

| Eye Drops (Oily) | |
|---|---|
| 3α-naphthyl-5-diethylcarbamoyl-1,2,4-oxadiazole | 0.1 % w/v |
| Castor oil | to 100 % |

The active ingredient was reduced to a fine state by sub-division to a particle size of less than 10µ. The castor oil was sterilised by heating in a hot air oven at 160° C. The active ingredient was sterilised and dispersed in the sterile castor oil to yield a homogeneous mixture.

EXAMPLE 72

| Eye Drops (aqueous) | |
|---|---|
| 5-diethyl carbamoyl-3-biphenylyl-1,2,4-oxadiazole | 0.1 % |
| Sodium chloride | 0.9 % |
| Phenyl ethanol | 0.4 % |
| Benzalknoium chloride | 0.002 % |
| Water (for injection) | to 100 % |
| Methyl cellulose | a sufficient amount to yield a final product with a viscosity of not less than 3000 centistokes. |

The methyl cellulose, sodium chloride, phenyl ethanol and benzalkonium chloride were dissolved in the water and sterilised by heating in a sealed container in an autoclave. The sterile micro-fine (particle size <10µ) active ingredient was then suspended in the sterile vehicle.

EXAMPLE 73

| Eye Ointment | | |
|---|---|---|
| 3α-naphthyl-5-diethylcarbamoyl-1,2,4-oxadiazole | | 0.1 % |
| Neomycin sulphate | | 0.5 % |
| Liquid paraffin | | 20.0 % |
| Soft paraffin | to | 100.0 % |

The paraffins were mixed, melted and strained, and were then sterilised by heating in a hot air oven at 160° C. The sterile micro-fine (particle size <10µ) active ingredient and neomycin sulphate were then suspended and homogeneously dispersed in the paraffin.

EXAMPLE 74

| Nasal Spray | | |
|---|---|---|
| 3α-naphthyl-5-diethylcarbamoyl-1,2,4-oxadiazole | | 0.1 % |
| Methyl cellulose | | 0.5 % |
| Glycerin | | 30.0 % |
| Sodium chloride | | 0.5 % |
| Nipa 82121 | | 0.05 % |
| Distilled water | to | 100.0 % |

The Nipa 82121, which is a mixture of the methyl, ethyl, propyl and butyl esters of para hydroxy benzoic acid, was dissolved in hot water, and the solution cooled to room temperature. The methyl cellulose, glycerin and sodium chloride were then dissolved in the Nipa 82121. The solution was clarified by filtration and the micro-fine active ingredient (particle size <10µ) suspended in it.

EXAMPLE 75

| Tablets | |
|---|---|
| 5-Diethylcarbamoyl-3-trans-methylsulphinylstyryl-1,2,4,-oxadiazole | 250 mg |
| Polyethylene Glycol 6000 | 7.5 mg |
| Magnesium Stearate | 2.5 mg |

The active ingredient is ground to a powder having a particle size between 1 and 10 microns. It is then granulated with the aid of a chloroform solution of the polyethylene glycol by passing it through a No. 12 mesh British standard sieve, and dried in vacuo. The dried granulate is passed through a No. 16 mesh British standard sieve. The granulate is then blended with the magnesium stearate which acts as a lubricant and compressed on 8 mm punches, preferably having a breakline. Each tablet weighs 260 mg. These tablets may if desired be film-coated in conventional manner.

We claim:

1. A compound selected from the group consisting of 3-adamantylcarbamoyl-1,2,4-oxadiazole, 5-diethylcarbamoyl-3-α-naphthyl-1,2,4-oxadiazole, 5-α-naphthyl-3-dimethylcarbamoyl-1,2,4-oxadiazole, 5-piperidinocarbonyl-3-p-methoxyphenyl-1,2,4-oxadiazole, 5-piperidinocarbonyl-3-α-naphthyl-1,2,4-oxadiazole, 5-dimethylcarbamoyl-3-α-naphthyl-1,2,4-oxadiazole, 5-di-n-propylcarbamoyl-3-α-naphthyl-1,2,4-oxadiazole and 3-biphenylyl-5-diethylcarbamoyl-1,2,4-oxadiazole.

2. A compound as claimed in claim 1, said compound being 3-adamantylcarbamoyl-1,2,4-oxadiazole.

3. A compound as claimed in claim 1, said compound being 5-diethylcarbamoyl-3-α-naphthyl-1,2,4-oxadiazole.

4. A compound as claimed in claim 1, said compound being 5-α-naphthyl-3-dimethylcarbamoyl-1,2,4-oxadiazole.

5. A compound as claimed in claim 1, said compound being 5-piperidinocarbonyl-3-p-methoxyphenyl-1,2,4-oxadiazole.

6. A compound as claimed in claim 1, said compound being 5-piperidinocarbonyl-3-α-naphthyl-1,2,4-oxadiazole.

7. A compound as claimed in claim 1, said compound being 5-dimethylcarbamoyl-3-α-naphthyl-1,2,4-oxadiazole.

8. A compound as claimed in claim 1, said compound being 5-di-n-propylcarbamoyl-3-α-naphthyl-1,2,4-oxadiazole.

9. A compound as claimed in claim 1, said compound being 3-biphenylyl-5-diethylcarbamoyl-1,2,4-oxadiazole.

* * * * *